United States Patent [19]

Alicot et al.

[11] 4,337,344

[45] Jun. 29, 1982

[54] PROCESS FOR THE PREPARATION OF DIBENZOTHIAZYL DISULFIDE

[75] Inventors: Michel J. C. Alicot, Lannemezan; Adrien P. N. Tignol, Montrejeau, both of France

[73] Assignee: PCUK Produits Chimiques Ugine Kuhlmann, Courbevoie, France

[21] Appl. No.: 62,398

[22] Filed: Jul. 31, 1979

[30] Foreign Application Priority Data

Aug. 18, 1978 [FR] France .................................. 78 24093

[51] Int. Cl.$^3$ .......................................... C07D 417/12
[52] U.S. Cl. ..................................... 548/158; 562/566
[58] Field of Search ......................... 548/158; 562/566

[56] References Cited

U.S. PATENT DOCUMENTS 2,024,567 12/1935 Clifford ............................... 548/158
2,024,575 12/1935 Gracia ................................. 548/158

OTHER PUBLICATIONS

Martell et al. "The properties and uses of Ethylenediamine Tetra Acetic Acid and its Salts", Bersworth Chemical Co. Framingham, Mass.

Primary Examiner—David B. Springer
Attorney, Agent, or Firm—Beveridge, DeGrandi and Kline

[57] ABSTRACT

A process for the preparation of dibenzothiazyl disulfide by oxidation of mercaptobenzothiazole in aqueous suspension by means of hydrogen peroxide, in which the oxidation is effected in the presence of ethylenediaminetetraacetic acid or an alkali metal salt derived therefrom.

7 Claims, No Drawings

PROCESS FOR THE PREPARATION OF DIBENZOTHIAZYL DISULFIDE

The present invention relates to a new process for the preparation of dibenzothiazyl disulfide which has the following formula:

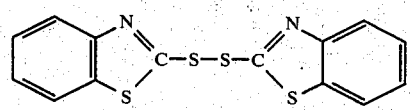

This product is largely used in particular as a vulcanization accelerator in the industry for the conversion of natural and synthetic rubbers; it may be used alone or in combination with other accelerators of the thiazole, thiuram or arylguanidine types.

In a general manner, the known processes of manufacture make use of the oxidation of mercaptobenzothiazole. They differ essentially from one another in the choice of oxidizing agent. Thus there have been recommended: nitric acid (U.S. Pat. No. 1,880,421 issued Oct. 4, 1932); nitrosyl chloride and nitric oxide (German Pat. No. 1,143,203 dated Aug. 14, 1963); sodium nitrate in acid medium (U.S. Pat. No. 3,062,825 issued Nov. 6, 1962); chlorine (French Pat. No. 2,174,052 dated Feb. 26, 1973); sodium hypochlorite (British Pat. No. 559,338 dated Feb. 15, 1944); and hydrogen peroxide in a mineral acid medium (U.S. Pat. Nos. 2,024,575 and 2,024,567 both issued Dec. 17, 1935). Some processes also make use of the direct oxidation of the mercaptobenzothiazole by oxygen in the presence of catalysts (for example, U.S. Pat. No. 3,654,297 issued Apr. 4, 1972).

Although these processes for the most part enable the dibenzothiazyl disulfide to be obtained with good yields, they may have disadvantages; their operation is not as easy as the simplicity of the reaction scheme might lead one to suppose.

There may be mentioned the processes making use of an alkali metal salt of mercaptobenzothiazole, an oxidizing salt, or a solvent medium other than water, or which necessitates (always in large proportions) the use of mineral acids.

The mother liquors which result from these processes are not generally able to be directly recycled without harm to the quality of the product and the yield, which necessarily involves expensive complementary treatments. When the rejection of the mother liquors is considered, it is necessary to take into account the strong chemical demand of the effluents for oxygen. The problems become of such complexity that these processes are no longer economically viable.

In other respects, the dibenzothiazyl disulfide obtained in a number of these processes further contains free mercaptobenzothiazole, which it is necessary to eliminate by a supplementary treatment, itself generating material for rejection.

It has now been found, according to the present invention, that it is possible to overcome these disadvantages. The process according to the invention, which comprises oxidizing the mercaptobenzothiazole in aqueous suspension by means of hydrogen peroxide, is characterized in that the oxidation is effected in the presence of ethylenediaminetetraacetic acid or of an alkali metal salt derived therefrom. Any of the alkali salts may be used although the sodium salt is preferred.

The granulometry or particle size of the mercaptobenzothiazole is between 5 and 200 microns, preferably between 10 and 100 microns. A higher granulometry would give rise to oxidation difficulties.

The concentration of mercaptobenzothiazole in the aqueous suspension comprises between 100 and 300 grams/liter; weaker concentrations needlessly reduce the productivity of the apparatus while stronger concentrations can cause difficulties in the handling of the reaction mixture.

The hydrogen peroxide, in molar excess of 5 to 30% with respect to the mercaptobenzothiazole, and preferably in molar excess of 10 to 20%, is used in the form of aqueous solutions, such that the usual commercial solutions titrate 50 or 70% of hydrogen peroxide per 100%.

With a view to the oxidation reaction, the ethylenediaminetetraacetic acid or one of its alkali metal salts is used at the rate of 0.025 to 1%, preferably 0.1 to 0.2% by weight with respect to the hydrogen peroxide expressed as 100%.

The oxidation can be effected at a temperature between 10° and 100° C., the range from 20° to 40° C. being preferred since the secondary reactions are quite negligible in this range.

The period of oxidation may be between 30 minutes and 50 hours; it is directly linked to the temperature and also to the excess of hydrogen peroxide. It is higher as the temperature is lower and the excess of hydrogen peroxide is smaller.

The dibenzothiazyl disulfide is formed in a substantially quantitative yield; it is isolated by any usual known means such as filtration or draining. It is obtained in a state of purity such that it is not necessary to carry out any purification treatment. In particular, the content of free mercaptobenzothiazole is less than 0.2-0.3%. The disulfide is formed of elementary particles of which the size ranges from 1 to 2 microns, united in agglomerates of from 30 to 50 microns; this physical aspect is quite satisfactory for applications in natural and synthetic rubbers and in particular permits a perfect dispersion.

The following examples illustrate the invention without being restricted thereto.

EXAMPLE 1

56 Liters of water, 11.5 grams of a dispersing agent of the ethylene oxide-fatty acid condensate type, 1.7 grams of the disodium salt of ethylenediaminetetraacetic acid and 14,820 kg of 100% merceptobenzothiazole are introduced with stirring into a previously passivated, stainless steel reactor of 100 liters capacity, provided with a stirring device, a temperature indicator and a double jacket enabling the temperature to be regulated. The temperature is taken to 35° C. and 1,770 kg of hydrogen peroxide at 100% in the form of a 70% solution are added in about fifteen minutes. The temperature is maintained at 35° C. and the mixture is left with stirring for 24 hours. The suspension obtained is filtered, and the filtrate is washed with 6 liters of water about five times, then drained and dried at a temperature of 80° to 100° C.

14,580 kg of dibenzothiazyl disulfide are obtained in the form of a cream-colored powder having a melting point (not corrected) of 172°–174° C., of which the content of free mercaptobenzothiazole is 0.15%.

The yield is 99% with respect to the mercaptobenzothiazole.

EXAMPLE 2

The procedure is as in Example 1, but instead of 56 liters of pure water, 56 liters of mother liquors from a previous operation are used; this volume corresponds to the whole of the mother liquors to which has been added the greater part of the wash water.

There are obtained, according to the same method of operation, 14,500 kg of dibenzothiazyl disulfide having a melting point (not corrected) of 172°–174° C. with a content of free mercaptobenzothiazole equal to 0.12%. The physical aspect, expecially the color of the product, is identical with that of the product obtained in Example 1.

The yield of dibenzothiazyl disulfide is 98.5% with respect to the mercaptobenzothiazole.

The method of operation, described in each of these examples, can be modified without difficulty with a view to continuous operation.

What is claimed is:

1. A process for the preparation of dibenzothiazyl disulfide by oxidation of an aqueous suspension of mercaptobenzothiazole by means of hydrogen peroxide, which consists in effecting the oxidation in the presence of ethylenediaminetetraacetic acid or an alkali metal salt thereof used at the rate of 0.025 to 1% by weight with respect to the hydrogen peroxide and at a temperature between 10° and 100° C.

2. The process as claimed in claim 1 in which the acid or the salt is used at the rate of 0.1 to 0.2% by weight with respect to the hydrogen peroxide.

3. The process as claimed in claim 1 in which the mercaptobenzothiazole has a granulometry of between 5 and 200 microns.

4. The process as claimed in claims 1 or 3 in which the concentration of mercaptobenzothiazole is between 100 and 300 g/l.

5. The process as claimed in claim 1 in which the hydrogen peroxide is present in a molar excess of from 5 to 30% with respect to the mercaptobenzothiazole.

6. The process as claimed in claim 1 in which the hydrogen peroxide is present in a molar excess of from 10 to 20% with respect to the mercaptobenzothiazole.

7. The process as claimed in claim 1 wherein it is carried out continuously.

* * * * *